United States Patent [19]

Franz et al.

[11] Patent Number: 4,496,389

[45] Date of Patent: Jan. 29, 1985

[54] AMIDE DERIVATIVES OF N-TRIFLUOROACETYL-N-PHOSPHONOMETHYLGLYCINE, HERBICIDAL COMPOSITIONS AND USE

[75] Inventors: John E. Franz, Crestwood; Robert J. Kaufman, University City, both of Mo.

[73] Assignee: Monsanto Company, St. Louis, Mo.

[21] Appl. No.: 609,263

[22] Filed: May 11, 1984

Related U.S. Application Data

[63] Continuation of Ser. No. 441,480, Nov. 15, 1982, abandoned, which is a continuation of Ser. No. 922,923, Jul. 10, 1978, Pat. No. 4,359,332.

[51] Int. Cl.$^3$ .......................... A61K 57/28; C07F 9/36
[52] U.S. Cl. ......................................... 71/86; 560/116; 560/121; 560/123; 560/124; 560/125; 560/169
[58] Field of Search ............... 560/116, 121, 123, 124, 560/125, 169; 71/86

[56] References Cited

U.S. PATENT DOCUMENTS

| 3,799,758 | 3/1974 | Franz | 71/86 |
| 3,853,530 | 12/1974 | Franz | 71/86 |
| 3,970,695 | 7/1976 | Rueppel | 260/935 |

*Primary Examiner*—Robert W. Ramsuer
*Attorney, Agent, or Firm*—David Bennett; Richard H. Shear

[57] ABSTRACT

This disclosure relates to alkyl N-trifluoroacetyl-N-phosphonomethylglycine amide and hydrazide derivatives, to herbicidal compositions containing same and to the herbicidal use thereof. These amide and hydrazide derivatives are useful as pre-emergent and/or post-emergent herbicides.

15 Claims, No Drawings

AMIDE DERIVATIVES OF N-TRIFLUOROACETYL-N-PHOSPHONOMETHYLGLYCINE, HERBICIDAL COMPOSITIONS AND USE

This is a continuation of application Ser. No. 441,480 filed Nov. 15, 1982, abandoned, which is itself a continuation of application Ser. No. 922,923 filed July 10, 1978, now U.S. Pat. No. 4,359,332.

This invention relates to alkyl N-trifluoroacetyl-N-phosphonomethylglycine amide and hydrazide derivatives, to herbicidal compositions containing same and to the herbicidal use thereof. More particularly, this invention relates to N-trifluoroacetyl-N-phosphonomethylglycinate esters having amide or hydrazide groups bonded to the phosphorus atom thereof.

In accordance with U.S. Pat. No. 3,970,695, issued July 20, 1976, N-perfluoroacyl-N-phosphonomethylglycines of the formula

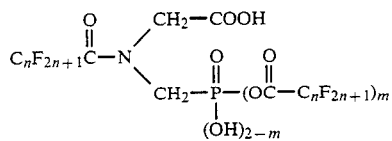

wherein n is an integer of from 1 to 4 and m is 1 or 0 are produced by reacting a perfluoroacyl anhydride with N-phosphonomethylglycine in the presence of a perfluoroalkanoic acid to form the compound of the formula wherein m is 1 and then by hydrolysis to form the compounds wherein m is 0.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530. Phenyl hydrazides of N-phosphonomethylglycine are disclosed in U.S. Pat. No. 3,972,915.

The novel N-trifluoroacetyl-N-phosphonomethylglycinate amide and hydrazide derivatives of this invention are those having the formula

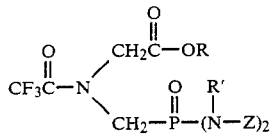 (I)

wherein R is an alkyl group of from 1 to 10 carbon atoms, a chloro lower alkyl group, a lower alkoxy lower alkyl group containing from 3 to 6 carbon atoms or a lower alkoxy lower alkoxy lower alkyl group containing from 5 to 9 carbon atoms, R' is hydrogen, lower alkyl, lower alkenyl or lower alkynyl, Z is a member of the class consisting of alkyl of from 1 to 6 carbon atoms, alkenyl of from 2 to 6 carbon atoms, alkynyl of from 3 to 6 carbon atoms, cycloalkyl containing from 3 to 7 carbon atoms or a

group wherein $R^2$ is lower alkyl, phenyl or substituted phenyl and $R^3$ is hydrogen or lower alkyl and together with the nitrogen atom R' and Z can form a heterocyclic ring.

As employed herein, "chloro lower alkyl" designates those alkyl groups containing up through four carbon atoms in a straight or branched chains and up to three chlorine groups. The terms "lower alkyl", "lower alkenyl", "lower alkynyl" and "lower alkoxy" as employed herein define such groups containing up to and including four carbon atoms.

Illustrative of the alkoxyalkyl groups which R represents are methoxyethyl, methoxypropyl, methoxybutyl, ethoxyethyl, ethoxypropyl, propoxyethyl, propoxypropyl and the like. Illustrative of the alkoxyalkoxyalkyl groups represented by R are, for example, methoxyethoxyethyl, methoxyethoxypropyl, methoxypropoxypropyl, methoxypropoxybutyl, ethoxyethoxyethyl, propoxypropoxypropyl and the like.

The novel compounds of this invention are produced by reacting an ester dichloride of N-trifluoroacetyl-N-phosphonomethylglycine having the formula

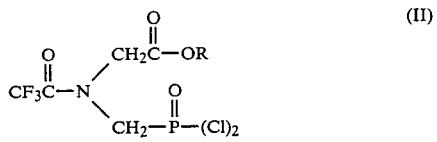 (II)

wherein R is as above-defined with an amine or hydrazine compound having the formula

wherein R' and Z are as above-defined in an organic solvent and in the presence of an amine hydrogen chloride acceptor under essentially anhydrous conditions at a temperature of from about 10° C. to about 50° C. preferably at ambient temperatures.

In producing the compounds of this invention by the above reaction, either an excess of the amine reactant or a tertiary amine can be employed as the hydrogen chloride acceptor. It is preferred to employ the hydrogen chloride acceptor in excess of stoichiometric to insure completeness of reaction. By the term "tertiary amine" as employed herein is meant tertiary alkylamines such as trimethylamine, triethylamine, tributylamine, trihexylamine and the like as well as aromatic tertiary amines such as pyridine, quinoline and the like.

The ratio of the reactants can vary over wide ranges. It is, of course, apparent to those skilled in the art that each chlorine atom in the N-trifluoroacetyl-N-phosphonomethylglycinyl dichloride will react with one amino or hydrazino group and that, therefore, one would employ the reactants in at least equivalent amounts. When employing amines or hydrazines which are volatile, it is sometimes desirable to employ an excess of the amine or hydrazine.

The substituted phenyl groups represented by $R^2$ are those containing up to 5 substituents selected from the group consisting of halogen, e.g., fluorine, chlorine and bromine; lower alkyl such as methyl, ethyl, propyl and butyl; and lower alkoxy such as methoxy, ethoxy, propoxy and butoxy groups and the like.

The nitrogen containing heterocyclic ring which R' and Z can be include, for example, ethyleneimine, trimethyleneimine, pyrrolidinyl, piperidinyl, morpholinyl, pyrrolyl, and the like.

The ester dichlorides of Formula II employed as a reactant in producing the compounds of this invention are prepared by reacting an ester of N-phosphonomethylglycine of the formula

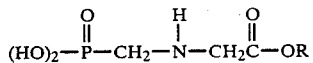

wherein R has the above-defined meaning with trifluoroacetic acid anhydride at temperatures of from about 10° C. to about 35° C., removing any excess anhydride and then treating the reaction product with excess thionyl chloride under refluxing conditions. The excess thionyl chloride is removed under vacuum to yield the dichlorides of Formula II.

The compounds of this invention are useful as herbicides.

The following non-limiting examples will serve to demonstrate to those skilled in the art the manner in which specific compounds within the scope of this invention can be prepared and their use as herbicides.

EXAMPLE 1

To a solution of ethyl N-trifluoroacetyl-N-(dichlorophosphonomethyl)glycinate (3.3 g, 0.01 mole) in 50 ml. of diethyl ether was added dropwise with good stirring 3 g (0.0423 mole) of pyrrolidine in 50 ml. of ether. After stirring at room temperature for 1½ hours, the reaction mixture was filtered and the filtrate was concentrated in vacuo to give 4.3 g of light brown viscous oil. This oil extracted with petroleum ether gave ethyl N-trifluoroacetyl-N-(dipyrrolidinophosphonomethyl)glycinate (3.75 g) as a slightly colored viscous oil, $N_D = 1.4500$.

Anal. Calc'd: C, 45.10; H, 6.32; N, 10.52. Found: C, 44,96; H, 6.24; N, 10.48.

EXAMPLE 2

To a solution of n-butylamine (3.1 g, 0.0423 mole) in 40 ml. of ether was added dropwise with stirring ethyl N-trifluoroacetyl-N-(dichlorophosphonomethyl)glycinate (3.3 g, 0.01 mole) in 50 ml. of ether. The reaction mixture was stirred for 2½ hours, then filtered and the filtrate was concentrated in vacuo to give a light yellow viscous oil. This oil was dissolved in petroleum ether, washed three times with water, dried over MgSO4, and concentrated in vacuo to give 3.3 g of ethyl N-trifluoroacetyl-N-(dibutylaminophosphonomethyl)glycinate, $N_D = 1.4429$.

Anal. Calc'd: C, 44.65; H, 7.26; N, 10.42. Found: C, 44.38; H, 7.08; N, 10.33.

EXAMPLE 3

To a solution of cyclohexylamine (14.6 g, 0.147 mole) in 100 ml. of ether was added dropwise with stirring ethyl N-trifluoroacetyl-N-(dichlorophosphonomethyl)-glycinate (11.55 g, 0.035 mole) in 200 ml. of ether. The reaction was stirred overnight at room temperature, then filtered and the filtrate concentrated in vacuo to yield a gum-solid. Upon trituration with petroleum ether, ethyl N-trifluoroacetyl-N-(bis(cyclohexylamino)-phosphonomethyl)glycinate (6.65 g) was obtained as a white solid, m.p. 118.5°–123° C.

Anal. Calc'd: C, 50.10; H, 7.30; P, 6.80. Found: C, 50.05; H, 7.23; P, 6.88.

EXAMPLE 4

To a solution of ethyl N-trifluoroacetyl-N-(dichlorophosphonomethyl)glycinate (3.3 g, 0.01 mole) in 75 ml. of tetrahydrofuran (distilled) was added dropwise with good stirring N-aminopiperidine (4.2 g, 0.0423 mole) in 20 ml. of tetrahydrofuran. The reaction was stirred overnight at room temperature, then filtered and the filtrate concentrated in vacuo to give an opaque oil. The oil was dissolved in ether, washed with water, dried over MgSO4, and concentrated to yield a glass which was recrystallized from hexane to yield ethyl N-trifluoroacetyl-N-(bis(N-aminopiperidino)-phosphonomethyl)glycinate, m.p. 106°–108° C.

Anal. Calc'd; C, 44.64; H, 6.83; P, 6.77. Found: C, 44.63; H, 6.73; P, 6.78.

EXAMPLE 5

To a solution of ethyl N-trifluoroacetyl-N-(dichlorophosphonomethyl)glycinate (3.3 g, 0.01 mole) in 50 ml. of tetrahydrofuran was added N-aminomorpholine (4.3 g, 0.042 mole) in 20 ml. of tetrahydrofuran. The reaction mixture was stirred overnight at room temperature, then filtered and concentrated in vacuo. The residue was washed with water to yield 0.4 g of material which was dissolved in chloroform and petroleum ether was added. Crystals of ethyl N-trifluoroacetyl-N-(bis(N-aminomorpholino)phosphonomethyl)glycinate formed, m.p. 69°–74° C.

Anal. Calc'd: N, 15.18; P, 6.71. Found: N, 14.97; P, 6.73.

EXAMPLE 6

To a solution of ethyl N-trifluoroacetyl-N-(dichlorophosphonomethyl)glycinate (3.3 g, 0.01 mole) in 25 ml. of tetrahydrofuran was added diallylamine (4.07 g, 0.042 mole) in 50 ml. of tetrahydrofuran. The mixture was stirred at room temperature overnight and was then filtered and the filtrate concentrated in vacuo. The residue was dissolved in ether, washed with water, 10% HCl, water, dried over MgSO4, and concentrated in vacuo. The residue was extracted with petroleum ether, and by concentrating the petroleum ether soluble material, ethyl N-trifluoroacetyl-N-(bis(diallylamino)phosphonomethyl)glycinate was obtained as a light yellow oil, $N_D = 1.4536$.

Anal. Calc'd: C, 50.55; H, 6.48; N, 9.31; P, 6.86. Found: C, 50.30; H, 6.60; N, 9.04; P, 7.08.

EXAMPLE 7

To a solution of ethyl N-trifluoroacetyl-N-(dichlorophosphonomethyl)glycinate (3.3 g, 0.01 mole) in 50 ml. of ether was added dimethylamine (2.03 g, 0.045 mole) in 50 ml. of ether. The reaction was stirred overnight at room temperature, then was filtered and the filtrate concentrated in vacuo. The residue was extracted into petroleum ether and the solution concentrated. The residue was dissolved in ether, washed with 3% NH4OH, dried over MgSO4, and concentrated in vacuo to yield ethyl N-trifluoroacetyl-N-(bis(dimethylamino)-phosphonomethyl)glycinate, $N_D = 1.5583$.

Anal. Calc'd: C, 38.04; H, 6.10; N, 12.10; P, 8.92. Found: C, 38.06; H, 6.18; N, 11.94; P, 8.79.

Anal. Calc'd: C, 48.21; H, 4.90; N, 14.79. Found: C, 48.37; H, 4.93; N, 14.92.

EXAMPLE 17

To a solution of dimethylhydrazine (5.04 g, 0.084 mole) in 75 ml. of ether was added dropwise with good stirring ethyl N-trifluoroacetyl-N-(dichlorophosphonomethyl)glycinate (6.93 g, 0.021 mole) dissolved in 120 ml. of ether. After stirring at room temperature overnight, the reaction mixture was filtered and the filtrate concentrated in vacuo. 6.4 g of the oil-glass residue was dissolved in fresh ether and washed with dilute $NH_4OH$, (then the dilute $NH_4OH$ washings were extracted three times with ether, and the ethereal layers were dried over $MgSO_4$, and finally concentrated to give 2.66 g solid product.) The solid was recrystallized from hexane to yield ethyl N-trifluoroacetyl-N-(bis(2,2-dimethylhydrazino)phosphonomethyl)glycinate, m.p. 84.5°–87.5° C.

Anal. Calc'd: C, 35.02; H, 6.14; N, 18.56; P, 8.21. Found: C, 35.13; H, 6.27; N, 18.49; P, 8.15.

EXAMPLE 18

To a solution of pentafluorophenylhydrazine (3.96 g, 0.02 mole) in 40 ml. of tetrahydrofuran at 0° C. was added over ½ hour ethyl N-trifluoroacetyl-N-(dichlorophosphonomethyl)glycinate (1.65 g, 0.005 mole) in 40 ml. of tetrahydrofuran. The reaction mixture was allowed to warm to room temperature and stir for 2 hours, then filtered. The filtrate was washed with water, dried, and concentrated in vacuo to yield a dark red-brown solid. This solid was washed several times with 70% ether in petroleum ether to yield ethyl N-trifluoroacetyl-N-(bis(pentafluorophenylhydrazino)phosphonomethyl)glycinate, m.p. 100°–110° C.

Anal. Calc'd: C, 34.93; H, 2.01; N, 10.72. Found: C, 34.88; H, 2.02; N, 10.63.

EXAMPLE 19

To a solution of p-methoxyphenylhydrazine hydrochloride (3.5 g, 0.02 mole) and triethylamine (4.04 g, 0.04 mole) in ether was added ethyl N-trifluoroacetyl-N-(dichlorophosphonomethyl)glycinate (3.3 g, 0.01 mole) dissolved in ether. Addition was carried out slowly and with good stirring. The reaction was allowed to stir overnight at room temperature. The reaction mixture was filtered and the filtrate concentrated in vacuo. The residue was taken up in ether, washed once with water, dried over $MgSO_4$, and concentrated in vacuo. Ethyl N-trifluoroacetyl-N-(bis(p-methoxyphenylhydrazino)phosphonomethyl)glycinate was obtained as a glass.

Anal. Calc'd: C, 47.28; H, 5.10; N, 13.13; P, 5.81. Found: C, 46.45; H, 4.70; N, 10.89; P, 5.77.

EXAMPLE 20

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 $kg/cm^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A — Canada Thistle* | K — Barnyardgrass |
| B — Cocklebur | L — Soybean |
| C — Velvetleaf | M — Sugar Beet |
| D — Morningglory | N — Wheat |
| E — Lambsquarters | O — Rice |
| F — Smartweed | P — Sorghum |
| G — Yellow Nutsedge* | Q — Wild Buckwheat |
| H — Quackgrass* | R — Hemp Sesbania |
| I — Johnsongrass* | S — Panicum Spp |
| J — Downy Brome | T — Crabgrass |

*Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1** | 4 | 11.2 | 2 | 3 | 2 | 2 | 3 | 2 | 3 | 1 | 3 | 1 | 3 |
| 1** | 4 | 5.6 | 2 | 2 | 2 | 2 | 4 | 3 | 2 | 1 | 2 | 1 | 3 |
| 2 | 4 | 11.2 | 2 | 2 | 1 | 3 | 4 | 0 | 3 | 2 | 3 | 3 | 3 |
| 2 | 4 | 5.6 | 2 | 2 | 1 | 2 | 2 | 0 | 2 | 1 | 1 | 2 | 3 |
| 3 | 4 | 11.2 | 1 | 1 | 1 | 2 | 4 | 2 | 1 | 1 | 1 | 1 | 2 |
| 3 | 4 | 5.6 | 0 | 1 | 1 | 2 | 3 | 2 | 1 | 1 | 1 | 1 | 2 |

EXAMPLE 8

To a solution of ethyl N-trifluoroacetyl-N-(dichlorophosphonomethyl)glycinate (6.6 g, 0.02 mole) in 200 ml. of ether was added dropwise with good stirring isopropylamine (4.9 g, 0.08 mole) in 70 ml. of ether. The reaction temperature was controlled by cold water bath. The reaction was stirred at room temperature overnight, then was filtered and the filtrate concentrated in vacuo. The residue was taken up in ether, washed with water, dried, concentrated in vacuo, extracted into hot petroleum ether and concentrated to give ethyl N-trifluoroacetyl-N-(bis(isopropylamino)phosphonomethyl)-glycinate as a light yellow oil-gum, $N_D = 1.4495$.

Anal. Calc'd: C, 41.60; H, 6.71; N, 11.20; P, 8.25. Found: C, 41.50; H, 6.86; N, 11.08; P, 8.09.

EXAMPLE 9

To a solution of ethyl N-trifluoroacetyl-N-(dichlorophosphonomethyl)glycinate (8.25 g, 0.025 mole) in 200 ml. of ether was added dropwise with stirring ethylamine (4.51 g, 0.10 mole) in 50 ml. of ether. The reaction was stirred at room temperature for several hours, then the reaction mixture was filtered and the filtrate concentrated in vacuo. The residue was dissolved in ether, washed with water, dried over MgSO$_4$, and concentrated in vacuo to give ethyl N-trifluoroacetyl-N-(bis(ethylamino)phosphonomethyl)-glycinate (4.45 g), $N_D = 1.4530$.

Anal. Calc'd: C, 38.04; H, 6.10; N, 12.10; P, 8.92. Found: C, 37.99; H, 6.10; N, 11.93; P, 8.84.

EXAMPLE 10

To a solution of ethyl N-trifluoroacetyl-N-(dichlorophosphonomethyl)glycinate (6.6 g, 0.02 mole) in 200 ml. of ether was added propylamine (4.7 g, 0.08 mole) in 50 ml. of ether. The reaction was stirred at room temperature for several hours, then the reaction mixture was filtered and the filtrate concentrated in vacuo. The residue was dissolved in 100 ml. ether, washed with water, dried over MgSO$_4$, and concentrated in vacuo to yield ethyl N-trifluoroacetyl-N-(bis(propylamino)phosphonomethyl)glycinate (5.1 g), $N_D = 1.4546$.

Anal. Calc'd: C, 41.60; H, 6.71; N, 11.20; P, 8.25. Found: C, 41.71; H, 7.02; N, 10.98; P, 8.42.

EXAMPLE 11

To a solution of butyl N-trifluoroacetyl-N-(dichlorophosphonomethyl)glycinate (7.9 g, 0.022 mole) in 200 ml. of ether was added slowly with good stirring allylamine (5.02 g, 0.088 mole) in 50 ml. of ether. The reaction was stirred overnight at room temperature, then was filtered, and the filtrate concentrated in vacuo. The residue was dissolved in ether, washed with water, dried over MgSO$_4$, and concentrated in vacuo to yield butyl N-trifluoroacetyl-N-(bis(allylamino)phosphonomethyl)glycinate (6.8 g), $N_D = 1.4624$.

Anal. Calc'd: C, 44.12; H, 6.42; N, 10.29; P, 7.58. Found: C, 44.00; H, 6.32; N, 9.87; P, 7.61.

EXAMPLE 12

To a solution of butyl N-trifluoroacetyl-N-(dichlorophosphonomethyl)glycinate (8.23 g, 0.023 mole) in ether was added dropwise with good stirring propargylamine (2.53 g, 0.046 mole) and triethylamine (4.65 g, 0.046 mole) in ether. The reaction was allowed to stir overnight at room temperature, and then was filtered and the filtrate concentrated in vacuo. The residue was taken up in ether, washed with water, dried over MgSO$_4$, and concentrated in vacuo to yield butyl N-trifluoroacetyl-N-(bis(2-propargylamino)phosphonomethyl)glycinate, $N_D = 1.4791$.

Anal. Calc'd: C, 45.57; H, 5.35; N, 10.63; P, 7.84. Found: C, 45.67; H, 5.30; N, 10.34; P, 7.99.

EXAMPLE 13

To a solution of 2-chloroethyl N-trifluoroacetyl-N-(dichlorophosphonomethyl)glycinate (8.2 g, 0.0225 mole) in 200 ml. of ether was added with good stirring dipropargylamine (4.2 g, 0.045 mole) and triethylamine (4.55 g, 0.045 mole) in 50 ml. of ether. The reaction was stirred at room temperature overnight, then the reaction mixture was filtered, and the filtrate concentrated in vacuo. The residue chromatographed through silica gel yielded 2-chloroethyl N-trifluoroacetyl-N-(bis(dipropargylamino)phosphonomethyl)glycinate (0.5 g), $N_D = 1.4899$.

Anal. Calc'd: C, 47.76; H, 4.22; N, 8.79. Found: C, 47.67; H, 4.33; N, 8.42.

EXAMPLE 14

To a solution of 2-methoxyethyl N-trifluoroacetyl-N-(dichlorophosphonomethyl)glycinate (7.45 g, 0.0207 mole) in 125 ml. of ether was added dropwise with good stirring butylamine (6.05 g, 0.083 mole) in 40 ml. of ether. The reaction was stirred at room temperature overnight, then the reaction mixture was filtered, and the filtrate concentrated in vacuo. The residue was dissolved in fresh ether, washed with water, dried over MgSO$_4$, and concentrated in vacuo to yield 2-methoxyethyl N-trifluoroacetyl-N-(bis(butylamino)phosphonomethyl)-glycinate (4.0 g), $N_D = 1.4572$.

Anal. Calc'd: C, 44.34; H, 7.21; N, 7.15. Found: C, 44.33; H, 7.05; N, 7.10.

EXAMPLE 15

To a solution of decyl N-trifluoroacetyl-N-(dichlorophosphonomethyl)glycinate (6.63 g, 0.015 mole) in 200 ml. of ether was added with good stirring cyclohexylamine (5.95 g, 0.06 mole) in 50 ml. of ether. The reaction was stirred overnight at room temperature, then filtered, and the filtrate concentrated in vacuo. The residue was dissolved in fresh ether, washed with water, dried over MgSO$_4$ and concentrated in vacuo. The residue was eluted through a dry column chromatograph with ethyl acetate to yield decyl N-trifluoroacetyl-N-(bis(cyclohexylamino)phosphonomethyl)glycinate, m.p. 79.5°–82.5° C.

Anal. Calc'd: C, 56.24; H, 8.74; N, 7.29. Found: C, 56.31; H, 8.82; N, 7.07.

EXAMPLE 16

To a solution of phenylhydrazine (4.5 g, 0.0423 mole) in 40 ml. of ether was added dropwise with good stirring ethyl N-trifluoroacetyl-N-(dichlorophosphonomethyl)glycinate (3.3 g, 0.01 mole) dissolved in ether. The reaction was stirred at room temperature for two hours, then filtered and the filtrate concentrated in vacuo to give a gum-solid. This was triturated with petroleum ether, then ether. The ether insoluble solid was washed with water to give ethyl N-trifluoroacetyl-N-(bis(phenylhydrazino)phosphonomethyl)glycinate (0.6 g), m.p. 113°–116° C. (glass), 143°–145° C. with decomposition.

TABLE I-continued

| Compound of Example No. | WAT | kg/h | A | B | C | D | E | F | G | H | I | J | K |
|---|---|---|---|---|---|---|---|---|---|---|---|---|---|
| 4 | 4 | 11.2 | 3 | 3 | 3 | 3 | 4 | 3 | 2 | 3 | 2 | 2 | 4 |
| 4 | 4 | 5.6 | 2 | 4 | 3 | 2 | 4 | 3 | 1 | 1 | 1 | 1 | 3 |
| 5 | 4 | 11.2 | 2 | 3 | 1 | 1 | 3 | 3 | 2 | 2 | 2 | 2 | 3 |
| 5 | 4 | 5.6 | 1 | 3 | 1 | 1 | 3 | 2 | 1 | 2 | 2 | 2 | 3 |
| 6 | 4 | 11.2 | 3 | 3 | 1 | 3 | 4 | 1 | 1 | 4 | 3 | 2 | 3 |
| 6 | 4 | 5.6 | 2 | 2 | 1 | 1 | 2 | 1 | 1 | 2 | 1 | 1 | 2 |
| 7 | 4 | 11.2 | 3 | 2 | 1 | 2 | 3 | 2 | 2 | 2 | 2 | 1 | 2 |
| 7 | 4 | 5.6 | 2 | 2 | 1 | 1 | 3 | 1 | 1 | 1 | 1 | 1 | 1 |
| 8 | 4 | 11.2 | 1 | 3 | 2 | 2 | 3 | 2 | 2 | 2 | 2 | 2 | 2 |
| 8 | 4 | 5.6 | 1 | 2 | 2 | 1 | 3 | 1 | 1 | 1 | 1 | 1 | 2 |
| 9 | 4 | 11.2 | 3 | 3 | 3 | 3 | 4 | 4 | 2 | 3 | 2 | 3 | 4 |
| 9 | 4 | 5.6 | 2 | 3 | 2 | 3 | 4 | 3 | 2 | 2 | 2 | 2 | 3 |
| 10 | 4 | 11.2 | 0 | 1 | 1 | 2 | 3 | 0 | 0 | 0 | 1 | 0 | 3 |
| 10 | 4 | 5.6 | 0 | 1 | 2 | 2 | 2 | 1 | 0 | 0 | 0 | 0 | 3 |
| 11 | 4 | 11.2 | 0 | 0 | 0 | 1 | 1 | 0 | 0 | 0 | 0 | 0 | 1 |
| 12 | 4 | 11.2 | 1 | 1 | 1 | 1 | 2 | 0 | 1 | 0 | 1 | 0 | 2 |
| 13 | 4 | 11.2 | 0 | 1 | 0 | 1 | 0 | 0 | 1 | 0 | 0 | 0 | 2 |
| 14 | 2 | 11.2 | 0 | 0 | 1 | 1 | — | 2 | 0 | 1 | 0 | 0 | 1 |
| 15 | 2 | 56 | 0 | 0 | 0 | 1 | 2 | 0 | 0 | 0 | 0 | 0 | 1 |
| 16 | 4 | 11.2 | 2 | 3 | 1 | 2 | 1 | 1 | 2 | 3 | 4 | 3 | 3 |
| 16 | 4 | 5.6 | 2 | 4 | 3 | 3 | 2 | 3 | 2 | 2 | 4 | 2 | 3 |
| 17 | 4 | 11.2 | 4 | 4 | 4 | 4 | 4 | 4 | 4 | 4 | 4 | 4 | 4 |
| 17 | 4 | 5.6 | 3 | 3 | 4 | 4 | 4 | 4 | 3 | 4 | 4 | 3 | 4 |
| 18 | 4 | 11.2 | 1 | 1 | 1 | 1 | 1 | 1 | 1 | 0 | 0 | 0 | 1 |
| 18 | 4 | 5.6 | 1 | 1 | 0 | 1 | 0 | 0 | 0 | 0 | 0 | 0 | 1 |
| 19 | 4 | 11.2 | 3 | 2 | 1 | 1 | 1 | 1 | 2 | 1 | 2 | 2 | 2 |
| 19 | 4 | 5.6 | 4 | 1 | 1 | 1 | 1 | 2 | 2 | 1 | 2 | 1 | 2 |

**Formulated just prior to spraying.

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1** | 4 | 1.12 | 0 | 1 | 1 | 0 | 1 | 1 | 0 | 2 | 0 | 0 | 0 | 1 | 0 | 2 | 2 | 2 |
| 2 | 4 | 5.6 | 2 | 1 | 2 | 1 | 3 | 2 | 1 | 2 | 1 | 3 | 2 | 1 | 3 | 2 | 2 | 3 |
| 2 | 2 | 1.12 | 1 | 0 | 1 | 0 | 1 | 2 | 1 | 1 | 1 | 0 | 0 | 0 | 1 | 0 | 0 | 2 |
| 2 | 2 | .28 | 0 | 0 | 0 | 0 | 0 | 0 | 0 | 0 | 0 | 0 | 0 | 0 | 0 | 0 | 0 | 2 |
| 4 | 4 | 5.6 | 3 | 3 | 2 | 4 | 3 | 3 | 2 | 2 | 2 | 4 | 3 | 3 | 2 | 3 | 3 | 3 |
| 4 | 4 | 1.12 | 2 | 1 | 1 | 1 | 2 | 2 | 1 | 2 | 1 | 3 | 2 | 1 | 2 | 3 | 3 | 3 |
| 4 | 4 | .28 | 1 | 0 | 0 | 0 | 1 | 1 | 1 | 1 | 0 | 0 | 0 | 0 | 1 | 2 | 2 | 2 |
| 5 | 4 | 5.6 | 3 | 3 | 4 | 3 | 3 | 3 | 1 | 2 | 2 | 3 | 3 | 2 | 3 | 4 | 3 | 4 |
| 6 | 4 | 5.6 | 2 | 2 | 2 | 1 | 3 | 3 | 2 | 2 | 2 | 3 | 3 | 2 | 2 | 4 | 3 | 4 |
| 6 | 4 | 1.12 | 1 | 2 | 1 | 1 | 1 | 2 | 1 | 2 | 2 | 2 | 2 | 1 | 0 | 2 | 2 | 3 |
| 6 | 4 | .28 | 1 | 1 | 0 | 0 | 1 | 1 | 1 | 1 | 0 | 2 | 1 | 1 | 0 | 2 | 2 | 2 |
| 7 | 4 | 5.6 | 2 | 2 | 2 | 1 | 3 | 3 | 1 | 2 | 2 | 3 | 3 | 2 | 2 | 3 | 3 | 3 |
| 7 | 4 | 1.12 | 1 | 1 | 1 | 1 | 2 | 1 | 1 | 1 | 1 | 1 | 1 | 1 | 1 | 2 | 2 | 2 |
| 8 | 4 | 5.6 | 2 | 3 | 3 | 2 | 3 | 4 | 4 | 2 | 2 | 4 | 4 | 3 | 3 | 4 | 3 | 4 |
| 8 | 4 | 1.12 | 1 | 1 | 1 | 1 | 2 | 1 | 1 | 1 | 1 | 3 | 1 | 1 | 1 | 2 | 2 | 3 |
| 9 | 4 | 5.6 | 2 | 4 | 3 | 3 | 3 | 2 | 2 | 3 | 3 | 3 | 3 | 4 | 3 | 4 | 4 | 4 |
| 9 | 4 | 1.12 | 1 | 1 | 1 | 1 | 1 | 2 | 1 | 2 | — | 2 | 2 | 1 | 1 | 3 | 3 | 3 |
| 10 | 4 | 5.6 | 1 | 0 | 0 | 0 | 3 | 2 | 0 | 2 | 1 | 1 | 0 | 0 | 1 | 3 | 0 | 1 |
| 10 | 2 | 1.12 | 0 | 0 | 0 | 0 | 1 | 1 | 0 | 0 | 0 | 1 | 0 | 0 | 1 | 0 | 0 | 0 |
| 16 | 4 | 5.6 | 3 | 4 | 4 | 4 | 4 | 4 | 2 | 3 | 2 | 4 | 4 | 3 | 3 | 4 | 4 | 4 |
| 16 | 4 | 1.12 | 1 | 1 | 3 | 2 | 4 | 3 | 1 | 2 | 1 | 2 | 2 | 3 | 3 | 4 | 4 | 4 |
| 16 | 4 | .28 | 0 | 0 | 2 | 0 | 2 | 1 | 0 | 2 | 0 | 1 | 1 | 2 | 1 | 2 | 2 | 2 |
| 17 | 4 | 5.6 | 3 | 4 | 4 | 4 | 4 | 4 | 3 | 3 | 3 | 4 | 3 | 4 | 4 | 4 | 4 | 4 |
| 17 | 4 | 1.12 | 1 | 3 | 4 | 4 | 3 | 3 | 1 | 2 | 1 | 2 | 2 | 3 | 4 | 4 | 3 | 4 |
| 17 | 4 | .28 | 0 | 0 | 1 | 1 | 2 | 2 | 0 | 2 | 0 | 0 | 0 | 1 | 3 | 4 | 2 | 3 |

**Formulated just prior to spraying.

EXAMPLE 21

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in the following table.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 1 | 2 | 11.2 | 3 | 0 | 0 | 0 | 1 | 0 | 1 | 1 | 1 | 0 | 0 |
| 2 | 2 | 11.2 | 1 | 3 | 0 | 0 | 2 | 0 | 0 | 0 | 0 | 0 | 0 |
| 3 | 2 | 11.2 | 1 | 0 | 0 | 0 | 0 | 0 | 1 | 0 | 0 | 0 | 0 |
| 4 | 2 | 11.2 | 1 | 0 | 0 | 0 | 0 | 0 | 0 | 1 | 0 | 0 | 0 |
| 5 | 2 | 11.2 | 2 | 0 | 0 | 0 | 2 | 0 | 1 | 3 | 0 | 0 | 0 |
| 6 | 2 | 11.2 | 3 | 0 | 0 | 0 | 0 | 0 | 0 | 0 | 0 | 0 | 0 |
| 7 | 2 | 11.2 | 1 | 0 | 0 | 0 | 0 | 0 | 0 | 1 | 0 | 0 | 0 |
| 8 | 2 | 11.2 | 0 | 0 | 0 | 0 | 0 | 0 | 1 | 1 | 0 | 0 | 0 |
| 9 | 2 | 11.2 | 3 | 3 | 0 | 0 | 1 | 1 | 0 | 1 | 1 | 0 | 0 |
| 12 | 2 | 11.2 | 0 | 0 | 0 | 0 | 2 | 1 | 0 | 3 | 0 | 1 | 3 |
| 14 | 2 | 11.2 | 1 | 0 | 0 | 0 | 0 | 0 | 0 | 0 | 0 | 0 | 0 |
| 16 | 2 | 11.2 | 2 | 0 | 0 | 0 | 0 | 0 | 0 | 0 | 0 | 0 | 0 |
| 17 | 2 | 11.2 | 3 | 0 | 0 | 0 | 0 | 0 | 0 | 0 | 0 | 0 | 0 |
| 18 | 2 | 11.2 | 1 | 0 | 0 | 0 | 0 | 0 | 0 | 1 | 0 | 0 | 0 |
| 19 | 2 | 11.2 | 1 | 0 | 0 | 0 | 0 | 0 | 1 | 2 | 1 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the aproximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

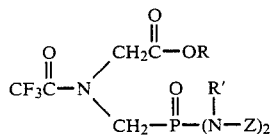

wherein R is an alkyl group of from 1 to 10 carbon atoms, a chloro lower alkyl group, a lower alkoxy lower alkyl group containing from 3 to 6 carbon atoms or a lower alkoxy lower alkoxy lower alkyl group containing from 5 to 9 carbon atoms, R' is hydrogen, lower alkyl, lower alkenyl or lower alkynyl, Z is a member of the class consisting of alkyl of from 1 to 6 carbon atoms, alkenyl of from 2 to 6 carbon atoms, alkynyl of from 3 to 6 carbon atoms, cycloalkyl containing from 3 to 7 carbon atoms.

2. A compound of claim 1 wherein R is lower alkyl.

3. A compound of claim 2 wherein Z is alkyl of from 1 to 6 carbon atoms, alkenyl of from 2 to 6 carbon atoms or alkynyl of from 3 to 6 carbon atoms.

4. A compound of claim 3 which is ethyl N-trifluoroacetyl-N-(bis(ethylamino)phosphonomethyl)-glycinate.

5. A compound of claim 3 which is ethyl N-trifluoroacetyl-N-(bis(cyclohexylamino)phosphonomethyl)glycinate.

6. A herbicidal composition comprising an inert adjuvant and a compound of the formula

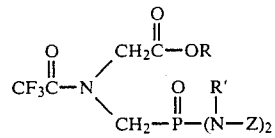

wherein R is an alkyl group of from 1 to 10 carbon atoms, a chloro lower alkyl group, a lower alkoxy lower alkyl group containing from 3 to 6 carbon atoms or a lower alkoxy lower alkoxy lower alkyl group containing from 5 to 9 carbon atoms, R' is hydrogen, lower alkyl, lower alkenyl or lower alkynyl, Z is a member of the class consisting of alkyl of from 1 to 6 carbon atoms, alkenyl of from 2 to 6 carbon atoms, alkynyl of from 3 to 6 carbon atoms, cycloalkyl containing from 3 to 7 carbon atoms.

7. A herbicidal composition of claim 6 wherein R is lower alkyl.

8. A herbicidal composition of claim 7 wherein Z is alkyl of from 1 to 6 carbon atoms, alkenyl of from 2 to 6 carbon atoms or alkynyl of from 3 to 6 carbon atoms.

9. A herbicidal composition of claim 8 wherein the compound is ethyl N-trifluoroacetyl-N-(bis(ethylamino)phosphonomethyl)glycinate.

10. A herbicidal composition of claim 8 wherein the compound is ethyl N-trifluoroacetyl-N-(bis(cyclohexylamino)-phosphonomethyl)glycinate.

11. A herbicidal method which comprises contacting a plant or the plant growth medium with a herbicidally effective amount of a compound of the formula

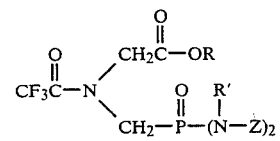

wherein R is an alkyl group of from 1 to 10 carbon atoms, a chloro lower alkyl group, a lower alkoxy lower alkyl group containing from 3 to 6 carbon atoms or a lower alkoxy lower alkoxy lower alkyl group containing from 5 to 9 carbon atoms, R' is hydrogen, lower alkyl, lower alkenyl or lower alkynyl, Z is a member of the class consisting of alkyl of from 1 to 6 carbon atoms, alkenyl of from 2 to 6 carbon atoms, alkynyl of from 3 to 6 carbon atoms, cycloalkyl containing from 3 to 7 carbon atoms.

12. A herbicidal method of claim 11 wherein R' is lower alkyl.

13. A herbicidal method of claim 12 wherein Z is alkyl of from 1 to 6 carbon atoms, alkenyl of from 2 to 6 carbon atoms or alkynyl of from 3 to 6 carbon atoms.

14. A herbicidal method of claim 13 wherein the compound is ethyl N-trifluoroacetyl-N-(bis(ethylamino)phosphonomethyl)glycinate.

15. A herbicidal method of claim 13 wherein the compound is ethyl N-trifluoroacetyl-N-(bis(cyclohexylamino)-phosphonomethyl)glycinate.

* * * * *